United States Patent [19]

Walt et al.

[11] Patent Number: 5,298,741
[45] Date of Patent: Mar. 29, 1994

[54] THIN FILM FIBER OPTIC SENSOR ARRAY AND APPARATUS FOR CONCURRENT VIEWING AND CHEMICAL SENSING OF A SAMPLE

[75] Inventors: David R. Walt, Lexington; Karen S. Bronk, Somerville, both of Mass.

[73] Assignee: Trustees of Tufts College, Medford, Mass.

[21] Appl. No.: 4,695

[22] Filed: Jan. 13, 1993

[51] Int. Cl.$^5$ .................. G01N 21/00; G02B 6/24; A61B 5/00
[52] U.S. Cl. .................. 250/227.23; 422/82.07; 422/82.06; 422/82.11; 436/172; 385/12; 128/634; 250/227.21
[58] Field of Search .............. 250/227.21, 227.23; 385/12, 13; 356/39, 40, 41; 128/634; 422/68.1, 82.05, 82.06, 82.07, 82.08, 82.09, 82.11; 435/808; 436/164, 172, 800, 805

[56] References Cited

U.S. PATENT DOCUMENTS

| | | | |
|---|---|---|---|
| Re. 31,879 | 5/1985 | Lübbers et al. | 436/133 |
| 4,144,452 | 3/1979 | Harte | 250/302 |
| 4,495,293 | 1/1985 | Shaffar | 436/172 |
| 4,822,746 | 4/1989 | Walt | 436/528 |
| 5,244,636 | 9/1993 | Walt et al. | 422/82.07 |

Primary Examiner—David C. Nelms
Assistant Examiner—John R. Lee
Attorney, Agent, or Firm—David Prashker

[57] ABSTRACT

The present invention provides a unique fiber optic sensor which is able to provide a visual examination of a sample and its surrounding environment concurrent with the ability to conduct chemical sensing and detection of at least one ligand of interest. The present invention also provides apparatus for making precise optical determinations and measurements for the ligand of interest which can be correlated with specific parameter or other ligands for specific applications and purposes.

15 Claims, 10 Drawing Sheets

THIN FILM FIBER OPTIC SENSOR ARRAY AND APPARATUS FOR CONCURRENT VIEWING AND CHEMICAL SENSING OF A SAMPLE

FIELD OF THE INVENTION

The present application is generally concerned with fiber optic sensors and light absorbing dyes which in combination are employed for qualitative and quantitative analytical determinations; and is specifically directed to the preparation and use of sensors capable of simultaneous chemical sensing measurements and visual imaging of the sample within its environment.

BACKGROUND OF THE INVENTION

The use of optical fibers and optical fiber strands in combination with light energy absorbing dyes for medical, biochemical, and chemical analytical determinations has undergone rapid development, particularly within the last decade. The use of optical fibers for such purposes and techniques is described by Milanovich et al. "Novel Optical Fiber Techniques for Medical Application", Proceedings of the SPIE 28th Annual International Technical Symposium on Optics and Electro-Optics, Volume 494, 1980; Seitz, W. R., "Chemical Sensors Based on Immobilized Indicators and Fiber Optics" in *C.R.C. Critical Reviews In Analytical Chemistry*, Vol. 19, 1988, pp. 135-173; Wolfbeis, O. S., "Fiber Optical Fluoresensors in Analytical Chemistry" in *Molecular Luminescence Spectroscopy, Methods and Applications* (S. G. Schulman, editor), Wiley & Sons, New York; Angel, S. M., Spectroscopy 2(4): 38 (1987); and Walt et al., "Chemical Sensors and Microinstrumentation", *ACS Symposium Series*, Volume 403, 1989, p. 252.

The optical fiber strands typically are glass or plastic extended rods having a small cross-sectional diameter. When light energy is projected into one end of the fiber strand (conventionally termed the "proximal end"), the angles at which the various light energy rays strike the surface are greater than the critical angle; and such rays are "piped" through the strand's length by successive internal reflections and eventually emerge from the opposite end of the strand (conventionally termed the "distal end"). Typically bundles of these strands are used collectively as optical fibers in a variety of different applications.

For making an optical fiber into a sensor, one or more light energy absorbing dyes are attached to the distal end of the optical fiber. The sensor can then be used for both in-vitro and/or in-vivo applications. As used herein, light energy is photoenergy and is defined as electromagnetic radiation of any wavelength. Accordingly, terms "light energy" and "photoenergy" include infrared, visible, and ultraviolet wavelengths conventionally employed in most optical instruments and apparatus; the term also includes the other spectral region of x-ray and microwave wavelengths (although these are generally not used in conjunction with optical fibers).

Typically, light from an appropriate energy source is used to illuminate what is chosen to be the proximal end of an optical fiber or a fiber bundle. The light propagates along the length of the optical fiber; and a portion of this propagated light energy exits the distal end of the optical fiber and is absorbed by one or more energy absorbing dyes. As conventionally used, the light energy absorbing dye may or may not be immobilized; may or may not be directly attached to the optical fiber itself; may or may not be suspended in a fluid sample containing one or more analytes of interest to be detected; and may or may not be retainable for subsequent use in a second optical determination.

Once the light energy has been absorbed by the dye, some light energy of varying wavelength and/or intensity returns through the distal end of the optical fiber and is conveyed through either the same fiber or a collection fiber or fibers to a detection system where the emerging light energy is observed and measured. The interactions between the light energy conveyed by the optical fiber and the properties of the light absorbing dye—in the presence of a fluid sample containing one or more ligands or analytes of interest and in the absence of any ligands or analytes whatsoever—provide an optical basis for both qualitative and quantitative determinations. Merely illustrating the use of optical fiber sensors presently known in a variety of conditions, apparatus, dyes and applications are U.S. Pat. No. 4,822,746; 4,144,452; 4,495,293; and Re. 31,879.

Most light detection systems employ a photosensitive detector such as a photodiode or photomultiplier tube. Spatial resolution of light is possible with two dimensional detectors such as video cameras and charge coupled devices. Moreover, in view of the microcircuitry and enhanced television technology presently available, a variety of light image processing and analytical systems have come into existence in order to both enhance, analyze and mathematically process the light energies introduced to and emerging from the absorbing dyes in such optical analytical techniques. Typically, these systems provide components for photon measurement and include image capture; data acquisitions; data processing and analysis; and visual presentation to the user. Commercial systems available today include the QX-7 image processing and analysis system sold by Quantex, Inc. (Sunnydale, CA); and the IM Spectrofluorescence imaging system offered by SPEX Industries, Inc. (Edison, N. J.). Each of these systems may be combined with microscopes, cameras, and/or television monitors for automatic processing of all light energy determinations.

Of the many different classes of light absorbing dyes which conventionally are employed with bundles of fiber strands and optical fibers for different analytical purposes are those compositions which emit light energy after absorption, termed "fluorophores"; and those which absorb light energy and internally convert the absorbed light energy rather than emit it as light, termed "chromophores." Fluorophores and fluorescent detection methods employing optical fibers are recognized as being markedly different and distinguishable from light energy absorbance and absorption spectroscopy.

Fluorescence is a physical phenomenon based upon the ability of some molecules to absorb light energy (photons) at specified wavelengths and then emit light energy of a longer wavelength and at a lower energy. Such emissions are called fluorescence if the emission is relatively long-lived, typically $10^{-11}$ to $10^{-7}$ seconds. Substances able to fluoresce share and display a number of common characteristics: the ability to absorb light energy at one wavelength or frequency; the reaching of an excited energy state; and the subsequent emission of light at another light wavelength and energy level. The absorption and fluorescence emission spectra are thus individual for each fluorophore; and are often graphically represented as two separate curves which are slightly overlapping. Also, all fluorophores demonstrate the Stokes' Shift—that is, the emitted light is always at a longer wavelength (and at a lower energy level) relative to the wavelength (and energy level) of the exciting light absorbed by the substance. Moreover, the same fluorescence emission spectrum is generally observed irrespective of the wavelength of the exciting light and, accordingly, the wavelength and energy of the exciting light may be varied within limits. Finally, fluorescence may be measured as the quantum yield of light emitted. The fluorescence quantum yield is the ratio of the number of photons emitted in comparison to the number of photons initially absorbed by the fluorophore. For more detailed information regarding each of these characteristics the following references are recommended: Lakowicz, J. R., *Principles of Fluorescence Spectroscopy*, Plenum Press, New York 1983; Freifelder, D., Physical Biochemistry, second edition, W. H. Freeman and Company, New York, 1982; "Molecular Luminescence Spectroscopy Methods and Applications: Part I" (S. G. Schulman, editor) in *Chemical Analysis*, Vol. 77, Wiley & Sons, Inc., 1985; *The Theory of Luminescence*, Stepanov and Gribkovskii, Iliffe Books, Ltd., London, 1968.

In comparison, substances which absorb light energy and do not fluoresce usually convert the light energy into heat or kinetic energy. The ability to internally convert the absorbed light energy identifies the dye as a "chromophore." Dyes which absorb light energy as chromophores do so at individual wavelengths of energy and are characterized by a distinctive molar absorption coefficient at that wavelength. Chemical analyses employing fiber optic strands and absorption spectroscopy using visible and ultraviolet light wavelengths in combination with the absorption coefficient allow for the determination of concentration for specific analytes of interest by spectral measurement.

Many of the recent improvements employing optical fiber sensors in both qualitative and quantitative analytical determinations concern the desirability of depositing and/or immobilizing various light absorbing dyes at the intended distal end of an optical fiber using a given technique or apparatus. In this manner, a variety of different optical fiber chemical sensors and methods have been reported for specific analytical determinations and applications such as pH measurement, oxygen detection, and carbon dioxide analyses. These developments are exemplified by the following publications: Freeman et al., *Anal. Chem.* 53:98 (1983); Lippitsch et al., *Anal. Chem. Acta.* 205:1, (1988); Wolfbeis et al., *Anal. Chem.* 60:2028 (1988); Jordan et al., *Anal. Chem.* 59:437 (1987); Lubbers et al., *Sens. Actuators* (1983); Munkholm et al., *Anal. Chem.* 58:1427 (1986); Seitz, W. R. *Anal. Chem.* 56:16A-34A (1984); Peterson et al., *Anal. Chem.* 52:864 (1980); Saari et al., *Anal. Chem.* 54:821 (1982); Saari et al., *Anal. Chem.* 55:667 (1983); Zhujun et al., *Anal. Chem.* 56:2199 (1984); Collison, M. E. and M. E. Meyerhoff, *Anal. Chem.* 62:425A (1990); Demas, O. N. and B. A. DeGraff, *Anal. Chem.* 63:809A (1991); Seitz, W. R., *CRC Crit. Rev. Anal. Chem.* 19:135 (1988); Kopelman et al., *Science* 258:778 (1992); Janata, J., *Anal. Chem.* 64:196R (1992); and Orella et al., *Anal. Chem.* 64:2210 (1992).

Despite these many innovations and developments, and without regard to whether the application is intended for in-vitro or in-vivo use, it has been nearly impossible to both view the sample or the surrounding environment and concurrently measure and detect a ligand or analyte of interest in a fluid sample using a single optical fiber sensor. Fiber sensors are usually single fibers, thereby precluding their use for imaging. On the other hand, imaging fibers and arrays have been employed only for their intended purpose—viewing. Thus, if viewing is desired, a separate optical fiber coherent bundle which is unencumbered and unobscured would be required in order to view the sample and its surroundings directly. Each of these chemical sensing fibers and visualization fibers markedly increases the size and complexity of the overall system such that no apparatus or system presently exists which both chemically senses and provides viewing capability concurrently. Accordingly, the development of a single imaging fiber optical sensor able to utilize a dye reagent for optical determinations of different ligands of interest, concurrently with a capability of viewing the sample and its environment at will, would be recognized as a major advance and substantial improvement.

SUMMARY OF THE INVENTION

The present invention is definable in alternative formats. A first definition provides a fiber optic sensor useful in an apparatus for concurrently viewing the environs of and optically detecting at least one ligand of interest of a fluid sample, said fiber optic sensor being comprised of:

a preformed, unitary fiber optic array comprising a plurality of individually clad, fiber optical strands disposed co-axially along their lengths and having two discrete optic array ends each of which is formed of multiple strand end faces, said preformed, unitary fiber optic array being of determinable configuration and dimensions, said two discrete ends of said preformed, unitary fiber optic array presenting two discrete optic array surfaces for introduction and conveyance of light energy; and a substantially uniform and uninterrupted thin film comprising at least one light energy absorbing dye positioned over one of said discrete optic array surfaces of said preformed, unitary fiber optic array, said thin film having a thickness ranging from about 1-50 microns, each light energy absorbing dye of said thin film reacting with a ligand of interest in a manner correlatable with an optical determination.

A second, alternative definition of the present invention provides an apparatus for concurrently viewing the environs of and optically detecting at least one ligand of interest of a fluid sample, said apparatus comprising;

a fiber optic sensor comprised of (a) a preformed, unitary fiber optic array comprising a plurality of individually clad, fiber optical strands disposed co-axially along their lengths and having two discrete optic array ends each of which is formed of multiple strand end faces, said preformed, unitary fiber optic array being of determinable configuration and dimensions, said two discrete ends of said unitary fiber optic array presenting two discrete optic array surfaces for introduction and conveyance of light energy.

(b) a substantially uniform and uninterrupted thin film comprising at least one light energy absorbing dye positioned over one of said discrete optic array surfaces of said preformed, unitary fiber optic array, said thin film having a thickness ranging from about 1-50 microns, each light energy absorbing dye of said thin film reacting with one ligand of interest in a manner correlatable with an optical determination;

means for placing said thin film of said fiber optic sensor into reactive contact with a fluid sample;

means for introducing light energy to said thin film of said fiber optic sensor for illumination of said light energy absorbing dye;

means for detecting emerging light energy from said illuminated thin film of said fiber optic sensor, said detected emerging light energy serving as an optical determination for a ligand of interest in the fluid sample;

means for illuminating the fluid sample and its environs; and means for concurrently viewing the fluid sample and its environs through said thin film of said fiber optic sensor.

A third, alternative definition of the present invention provides a method for concurrently viewing the environs of and optically detecting at least one ligand of interest of a fluid sample, said method comprising the steps of:

obtaining a fiber optic sensor comprised of
(a) a preformed, unitary fiber optic array comprising a plurality of individually clad, fiber optical strands disposed co-axially along their lengths and having two discrete optic array ends each of which is formed of multiple strand end faces, said preformed, unitary fiber optic array being of determinable configuration and dimensions, said two discrete ends of said preformed, unitary fiber optic array presenting two discrete optic array surfaces for introduction and conveyance of light energy.
(b) a substantially uniform and uninterrupted thin film comprising at least one light energy absorbing dye and positioned over one of said discrete optic array surfaces of said preformed, unitary fiber optic array, said thin film having a thickness ranging from about 1-50 microns, each light energy absorbing dye of said thin film reacting with one ligand of interest in a manner correlatable with an optical determination;

placing said thin film of said fiber optic sensor into reactive contact with a fluid sample;

introducing light energy to said thin film of said fiber optic sensor for illumination of said light energy absorbing dye;

detecting emerging light energy from said thin film of said fiber optic sensor, said detected emerging light energy serving as an optical determination for a ligand of interest in the fluid sample;

illuminating the fluid sample and its environs: and concurrently viewing the fluid sample and its environs through said thin film of said fiber optic sensor.

BRIEF DESCRIPTION OF THE FIGURES

The present invention may be more easily and completely understood when taken in conjunction with the accompanying drawing, in which.

DETAILED DESCRIPTION OF THE INVENTION

Figure 1:
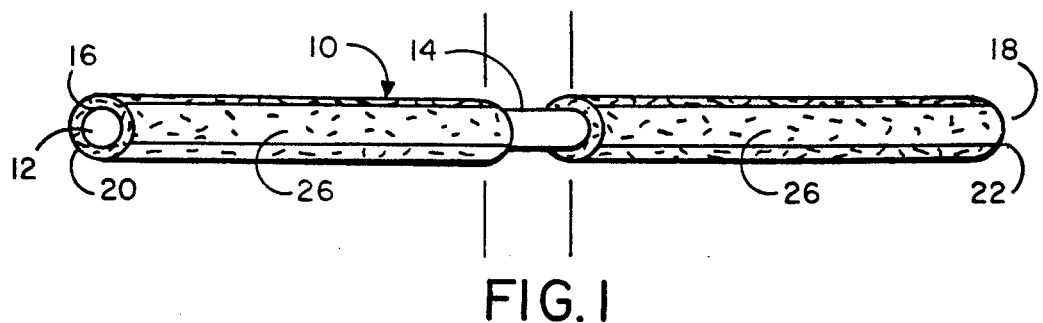
FIG. 1 is an overhead view of a preferred, individually clad, fiber optical strand.

The present invention is a marked improvement in fiber optic sensors; apparatus, systems and assemblies; and in methods for viewing a sample within its surroundings and for performing qualitative and/or quantitative optical measurements using a unique fiber optic sensor. The physical construction of this singular fiber optic sensor and the manner of its making are the critical and demanding aspects of the invention. The apparatus, methods for making optical determinations, and systems of qualitative and quantitative detection subsequently described are based and rely upon the existence and use of the unique fiber optic sensor as an essential component.

Although the unique fiber optic sensor and the other aspects of the present invention may bear a superficial similarity to conventionally known optical fibers, fiber optic strands, and fluorometric and colorimetric optical systems for making analytical determinations, it will be recognized and appreciated that the present invention provides multiple benefits and major advantages not previously available heretofore. These include:

1. A fully constructed fiber optical sensor comprising a preformed, unitary fiber optic array composed of individually clad, fiber optical strands disposed co-axially along their lengths and which has a thin film comprising at least one light energy absorbing dye positioned over, although not necessarily deposited on, one end surface of the optic array. This unique fiber optic sensor permits the use of one or more chemical sensing dyes to measure different ligands indicative of parameters such as pH, oxygen, carbon dioxide and the like and concurrently offer the capabilities of viewing the fluid sample and its environs. Such a single, discrete imaging fiber optic array, in so far as is presently known, has never before been constructed.

2. Different in-vitro measurements and analytical determinations may now be made using a single fiber optic sensor prepared in accordance with the present invention. The in-vitro applications and assay optical measurements may be performed concurrently with viewing and direct observation of one or multiple fluid samples. Each concurrently conducted measurement or determination for a ligand of interest is made individually, accurately, and precisely. The observed images and empirical results are then presented and/or computed individually to provide precise information regarding the sample as it is empirically found or situated in-vitro.

3. The unique fiber optic sensor as well as the apparatus and measurement procedures described hereinafter may also be employed in a variety of different in-vivo conditions with both humans and animals. The present invention not only provides accurate and rapid measurements and optical determinations, but also offers a direct visualization of the environment in which the analyzed samples exist--using a single discrete fiber optic sensor rather than the conventional bundle of different fiber strands joined together for limited purposes. The present invention thus provides a minimum-sized diameter sensor for in-vivo catherization; a minimum intrusion into the bloodstream or tissues of the living subject for assay purposes; and a minimum of discomfort and pain to the living subject. The sensors also provide optical precision and the reliability of direct observation as well as ligand detection and measurement in both qualitative and/or quantitative terms.

4. The present invention provides a fiber optic sensor suitable for use with multiple light systems and apparatus; and is also suitable for use with two or more light energy absorbing dye compositions which do not present completely overlapping spectral properties. Thus, the present invention may be prepared and employed with any measurable range of light energy or wavelengths which can be conveyed or propagated through a fiber optic strand including infrared light, visible light and ultraviolet light wavelengths. The diversity of uses and applications for the sensor is limited only by the choice of light energy absorbing dye(s) available from the entirety of those conventionally known today. In addition, dyes may be combined with enzymes and/or antibodies to alter or expand selectivity.

5. The present invention optionally permits the user to employ the unique fiber optic sensor in a fully automated, monitored, and preferably computerized system. A number of alternative apparatus formats are possible and suitable. The goal of all these automated systems is to provide the user with an apparatus that can detect and display light of varying intensity and wavelengths nearly simultaneously. Typically, such systems are of two general types: phototubes and charge coupled devices (or "CCD's"). A conventional constructed camera is but one example of such automated apparatus; and in an extreme case, even the detection elements in the camera could be used alone.

In one desirable apparatus format, the unique optic fiber sensor is employed with a microscope objective, a camera, a visual monitor, and a computerized image processing and analytical program. In this embodiment providing a fully automated, computer-controlled processing apparatus and measurement system, the intensity and wavelength of light energy is carefully controlled; the light energy is introduced to the fiber optic sensor at specifically controlled occasions and durations; and the resulting optic images and emerging light photons conveyed for visualization and/or analytical measurement are mathematically processed and correlated via computer programs into immediately useful data and often visualized on a television monitor or other display apparatus by using such fully automated, computerized apparatus and analytical systems. Not only is the optical determination made and a direct viewing conducted of a single fluid sample rapidly and reproducibly; but also many different fluid samples may be observed and analyzed individually seriatim for detection of a ligand of interest and/or visual imaging concurrently—each individual fluid sample following its predecessors in series.

6. The fiber optic sensor of the present invention also may be constructed in two different structural forms, thereby allowing for either near-field viewing or far-field viewing of the sample and its environs. Near-field viewing is conventionally recognized and defined as a focused observation distance and clear image representation of only a few microns (typically 1–10 microns) from the distal array surface of the fiber optic array. Alternatively, far-field viewing is conventionally recognized and defined as a focused distance of direct observation and clear visualization of items beyond the near-field and extending forward up to several centimeters (typically up to about 3–4 centimeters) distance from the distal optic array surface. Far-field viewing requires the presence and rigid attachment of a focusing objective lens such as a gradient index lens (or "GRIN" lens) to the distal array surface of the unitary fiber optic array. Near-field viewing can be obtained without a GRIN lens or using a GRIN lens with a focal point at its surface.

The fiber optic sensor disclosed herein offers the user the opportunity to select and choose the nature of the observation and visualization—that is, either near-field or far-field viewing. The sensor is then constructed to accommodate the intended application and expected distances of the objects, items, or sample environments to be viewed.

Since the present invention is definable in multiple formats and may be employed in different modes for a variety of divergent purposes and applications, the subject matter as a whole which is the present invention will be presented and described individually as component parts and then collectively as assemblies in order that the prospective user may more quickly recognize and appreciate their major differences and distinctions in comparison to the fiber optic apparatus and systems conventionally known.

I. The Organization and Construction of the Fiber Optic Sensor

The unique fiber optic sensor comprises two, and optionally three, components: a preformed, unitary fiber optic array comprised of a plurality of individually clad fiber optical strands disposed co-axially along their lengths; a thin film comprising one or more light energy absorbing dyes positioned over one optic surface of the array; and optionally, a "GRIN" lens joined to and optically aligned with the fiber optic array. Each component will be described in detail.

A. The Preformed, Unitary Fiber Optic Array

The unique fiber optic array, its organization and construction, and its component parts are illustrated by FIGS. 1-6 respectively. Each discrete, unitary fiber optic array is a preformed bundle comprised of a plurality of individually clad, fiber optical strands disposed coaxially along their lengths. The smallest common repeating unit within the preformed array is thus a single fiber optical strand. The manner in which these optical fiber strands are prepared and the manner in which these prepared optical strands are joined collectively into an organized optic array are conventionally known, but are fundamental to a proper understanding and use of the present invention.

The Individually Clad, Optical Fiber Strand

Figure 2A:
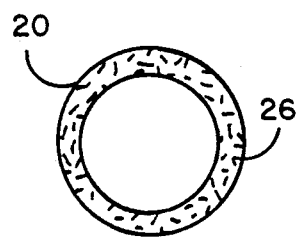
FIGS. 2A and 2B are views of the proximal and distal surfaces of the fiber optical strand of FIG. 1.
Figure 2B:
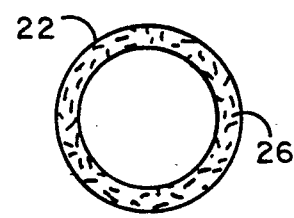

A preferred optical fiber strand is illustrated by FIGS. 1 and 2A and 2B. As seen therein, an individual optical fiber strand 10 is comprised of a single optical fiber 12 having a rod-like shaft 14 and two fiber ends 16, 18, each of which provides a substantially planar end surface. The intended distal surface 20 at the fiber end 16 is illustrated by FIG. 2A while the intended proximal surface 22 at the fiber end 18 is illustrated within FIG. 2B. It will be recognized and appreciated that the terms "proximal" and "distal" are relative and interchangeable until the strand is ultimately positioned in an apparatus. The optical fiber 12 is composed typically of glass or plastic; and is a flexible rod able to convey light energy introduced at either of its ends 16 and 18. Such optical fibers 12 are conventionally known and commercially available. Alternatively, the user may himself prepare individual optical fibers in accordance with the practices and techniques reported in the scientific and industrial literature. Accordingly, the optical fiber 12 is deemed to be conventionally known and available as such.

It will be appreciated that FIGS. 1-2 are illustrations in which the features have been purposely magnified and exaggerated beyond their normal scale in order to provide both clarity and extreme detail. Typically, the conventional optical fiber has a cross section diameter of 5-500 micrometers; and is routinely employed in lengths ranging between meters (in the laboratory) to kilometers (in field telecommunications). Moreover, although the optical fiber 12 is illustrated via FIGS. 1-2 as a cylindrical extended rod having substantially circular proximal and distal end surfaces, there is no requirement or demand that this specific configuration be maintained. To the contrary, the optical fiber may be polygonal or asymmetrically shaped along its length; provided with special patterns and shapes at the proximal and/or distal faces; and need not present an end surface which is substantially planar. Nevertheless, for best efforts, it is presently believed that the substantially cylindrical rod-like optical fiber having planar end surfaces is most desirable.

Each optical fiber 12 is desirably, but not necessarily, individually clad axially along its length by cladding 26. This cladding 26 is composed of any material with a lower refractive index than the fiber core and prevents the transmission of light energy photons from the optical fiber 12 to the external environment. The cladding material 26 may thus be composed of a variety of radically different chemical formulations including various glasses, silicones, plastics, platings, and shielding matter of diverse chemical composition and formulation. The manner in which the optical fiber 12 is clad is also inconsequential and of no importance to the present invention. Many methods of deposition, extrusion, painting and covering are scientifically known and industrially available; and any of these conventionally known processes may be chosen to meet the requirements and convenience of the user. Moreover, the quantity of cladding employed need only be that minimal amount which effectively prevents light energy conveyed by the optical fiber 12 from escaping into the ambient environment. It will be recognized and appreciated therefore, that the depth of cladding 26 as appears within FIGS. 1 and 2 respectively is greatly exaggerated and purposely thickened in appearance in order to show the general relationship; and is without scale or precise ratios between the cladding 26 and the optical fiber 12.

It will also be recognized that the configuration of the cladding 26 as shown by FIGS. 1 and 2 has been shaped as a circular coating to illustrate a preferred embodiment only. For reasons as will become clear subsequently, it is desirable that the cladding 26 take form in regular geometric form as a round or circular shape. The illustrated configuration, however, is merely a preferred embodiment of the cladding 26 as it extends co-axially along the length of the optical fiber 12. For purposes of added clarity also, FIG. 1 reveals the individually clad, optical fiber strand 10 in partial cross-section to demonstrate the relationship between the optical fiber core 12 and the cladding 26 which is coextensive along its length.

Figure 3A:
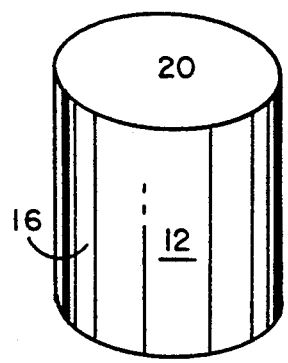
FIGS. 3A and 3B are alternative constructions of the optical end surface for the fiber optical strand of FIG. 1.
Figure 3B:
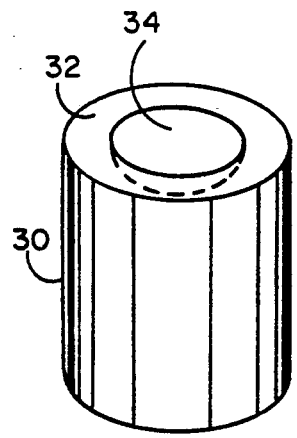

The user also has a variety of choices at his discretion regarding the configuration of the "distal" end 16 of the optical fiber 12 as shown by FIGS. 3A and 3B; however, both ends of the strand must be the same—i.e., if the "distal" end is cylindrical then the "proximal" end must be also. As seen in FIG. 3A, the "distal" end 16 is substantially cylindrical in shape and desirably presents a surface 20 which is substantially planar and smooth. A possible, but less desirable, alternative is shown by FIG. 3B, in which the distal end 30, nevertheless provides a very different end surface for the optical fiber 12. The surface 32 includes a depression or well 34 which extends into the substance of the optical fiber 12 at a depth typically of several micrometers. Although the well 34 appears substantially circular within FIG. 3B, oval or other rotund configured depressions may also be employed as fits the needs or convenience of the use. Similarly, the void volume of the well 34 from its greatest depth to the proximal surface 32 may also be varied.

It will be recognized and appreciated as well that the range and variety of dimensional and configurational divergence for the strand end is limited only by the user's ability to subsequently dispose and immobilize a thin film of dye composition/formulation of controlled thickness on the intended distal surface of the optical fiber 12. In some embodiments, a greater depth of film on the surface of the distal end surface may be highly desirable; nevertheless, for most general assay purposes, both quantitative and qualitative, the intended distal surface illustrated within FIG. 3A as a substantially planar and smooth surface is deemed to be most suitable and desirable.

For general construction of the fiber optic sensor and for most purposes and applications of the improved optical detecting system and procedures described hereinafter, it is desirable to employ the individually clad, fiber optical strand illustrated by FIGS. 1, 2A, 2B in preference to a bare, unsheathed strand. Clearly, the optical fiber is unable to transmit light energy photons to any other fiber or strand due to the cladding material 26 which forms a sheath. This sheath, having a refractive index less than the strand core, prevents loss of light energy photons into the general environment. Accordingly, the potential for photon loss, distortion, or other optical error is minimized and reduced. For these reasons, the individually clad optical fiber mode of construction is preferable to the use of bare optical fiber strands in order to achieve greater precision and accuracy.

The Preformed, Unitary Array

While the single repeating unit comprising the preformed fiber optic sensor is the individually clad, fiber optic strand described previously, it is the organizational positioning and alignment of the many, individually clad, fiber optic strands as a unitary array which is an essential component of the invention. A typical coherent fiber optic array is illustrated by FIGS. 4–6 respectively.

Figure 4:
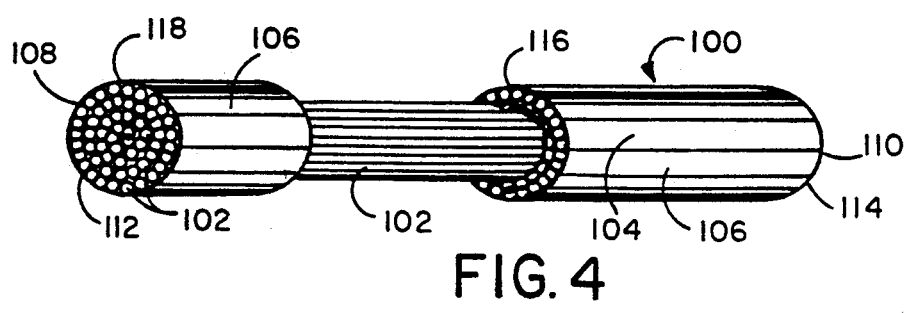
FIG. 4 is an overhead view of a preformed, unitary fiber optical array using the fiber optic strand of FIG. 1.

The unitary fiber optical array 100 appears in exaggerated, highly simplified views without regard to scale within FIG. 4. The preformed array is composed of a plurality of individually clad, fiber optical strands which collectively lie co-axially along their respective lengths as the discrete, unitary optic array 104 of fixed and determinable configuration and dimensions. The optic array 104 has a unitary, rod-like collective body 106 and intended distal and proximal collective ends 108, 110 formed of multiple strand end faces. The intended distal collective end 108 provides a substantially planar and smooth optic array provides an optic array surface 114. The topographical surface 116 is the result of fusing the clad of each fiber optical strand 102 collectively with a filler material 118 such that the fusion is drawn and appears as a discrete, unitary array. In this manner, the exterior surface 116 of the collective array body 106 may be configured and dimensioned as an assembly in an acceptable manner and useful manner. It will be recognized and appreciated also that a substantially cylindrical configuration and topography is maintained and presented by the unitary imaging fiber optic array 100 merely as one preferred embodiment. Any other regular or irregular configuration and design may be achieved and employed to satisfy the individual user's needs or desires.

Figure 5:
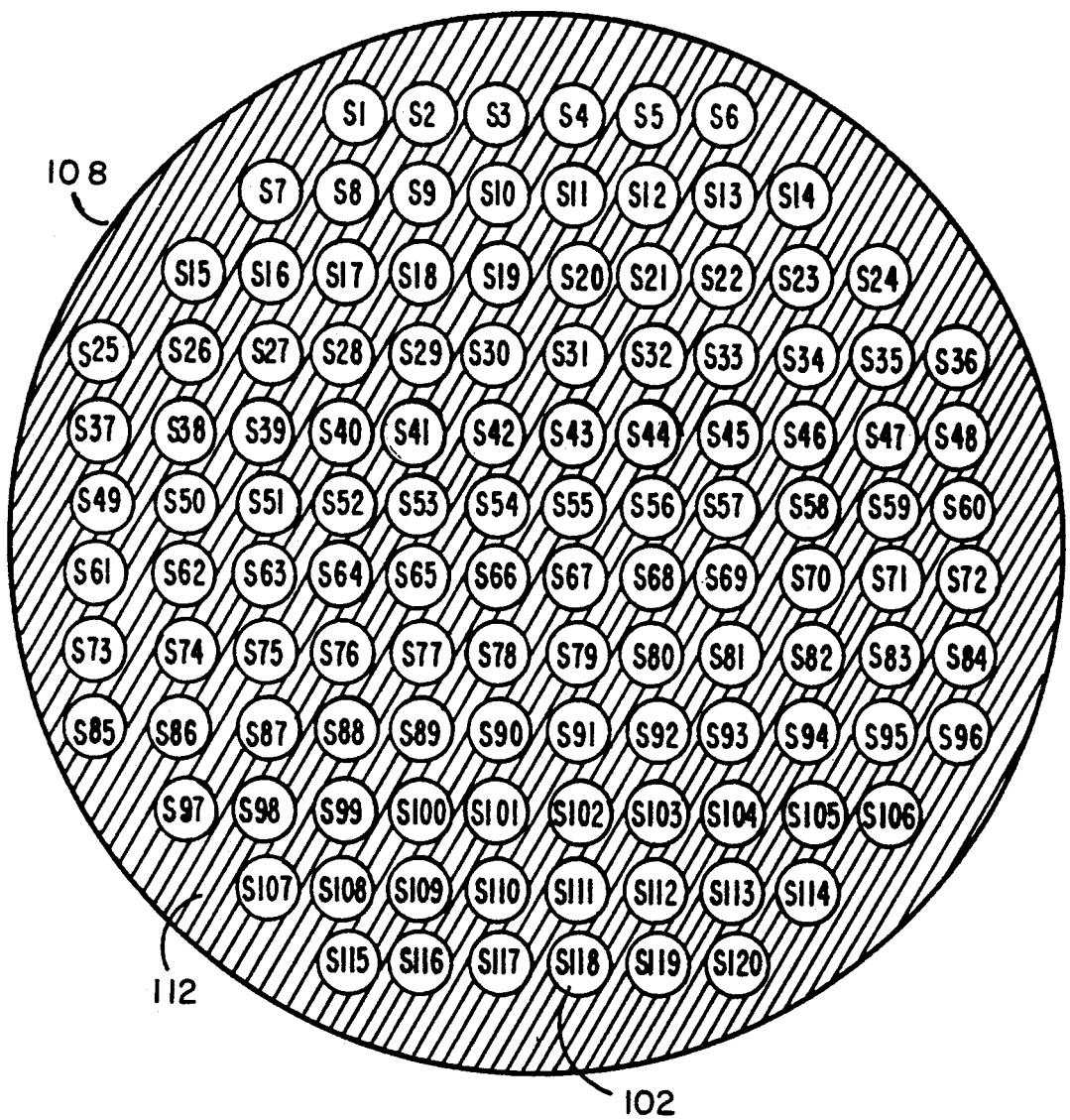
FIG. 5 is a view of the intended distal optical array surface of the unitary fiber optic array of FIG. 4.
Figure 6:
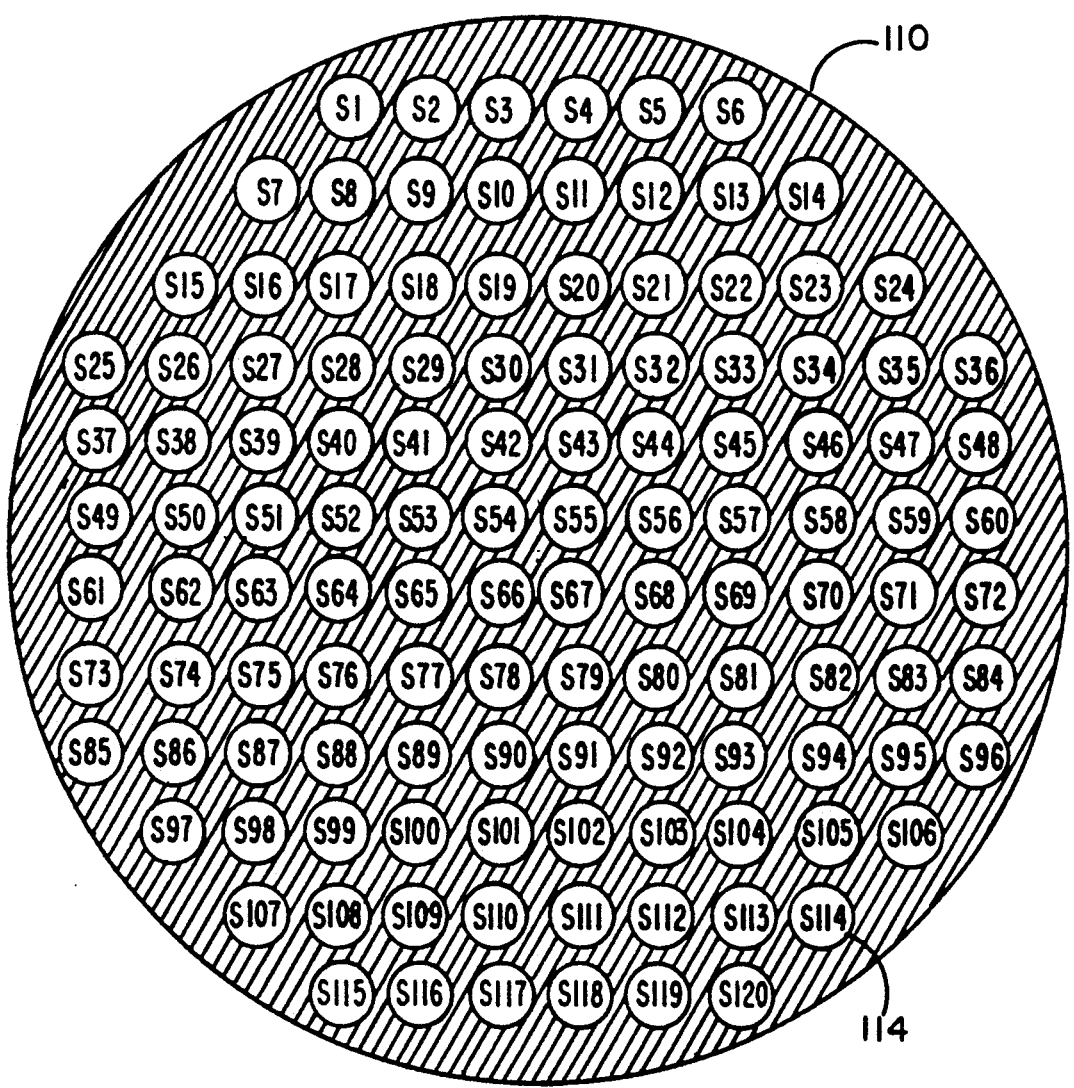
FIG. 6 is a view of the intended proximal optical array surface of the unitary fiber optic array of FIG. 4.

For purposes of clarity and ease of understanding, FIGS. 5 and 6 present a very limited and greatly reduced number of individually clad, fiber optical strands 102 present within the preformed optical array 104. A total of only 120 individually clad, fiber optical strands are seen to comprise the optical array 104 in greatly magnified and scale-exaggerated views. Moreover, the relationship of the optical array surface 112 (the intended distal end) with respect to the other optical array surface 114 (the intended proximal end) becomes simplified and more-readily appreciated when using this limited number of 120 optical fiber strands. In practice and reality, however, it is estimated that typically there are 2000-3000 optical fiber strands in a conventional array of 200 μm diameter. Thus the true total number of individually clad, fiber optic strands forming the unitary imaging fiber optic array will typically be in the thousands and vary substantially with the cross-sectional diameter of each optical fiber and the thickness of the cladding material employed when constructing the optical fiber strands themselves.

The construction, organization, and positional alignment within a typical fiber optical unitary array is revealed by FIGS. 4–6. For descriptive purposes only, each of the individually clad, optical fiber strands is presumed to be linearly straight in position and has been arbitrarily assigned an identifying number S1-S120 as shown via FIGS. 5 and 6. The intended distal optic array surface 112 of FIG. 5 and the intended proximal optic array surface of FIG. 6 together show that each of the individual fiber optical strands S1-S120 can be identified and distinguished from its adjacently disposed neighbor as well as from any other optical fiber strand within the preformed array 104.

It will be recognized and appreciated also that the overall organization of the individually clad, optical fiber strands 102 within the unitary array 100 is as aligned and parallel strands which maintain their relative organizational positioning in a coherent, consistently aligned manner over the entire length of the collective body 106. This is deemed to be the most desirable and most easily constructable organization scheme for the preformed optical fiber array of the present invention.

Although this highly organized, coherent, and rigidly aligned collective construction is deemed to be most desirable, this high degree of organizational alignment is not an absolute requirement for each and every embodiment of the unitary optical array. Alternative manufacturing practices allow for a more random disposition of the individually clad, optical fiber strands disposed co-axially along their lengths. Although less desirable, a partially random disposition and a completely random alignment of the optical fiber strands will also result in a unitary collective body of optical fibers and in proximal and distal collective ends which provide two discrete optical array surfaces. It will be recognized therefore that while the individually clad, optical fiber strands may lie adjacent one another at one end, they may deviate and meander through the length of the array such that their position relative to one another may vary substantially in part or in whole—thereby creating semi-coherent or incoherent positional alignments which vary in the randomness of their organizational construction. There is no requirement that the positioning of the intended proximal end of one strand be aligned and/or identical with the positioning of the intended distal end within the unitary optic array.

The entirety of the construction for the unitary optical fiber array (whether uniformly coherent, semi-random, or completely randomly organized) provides a means of introducing light energy photons of any determinable wavelength at one optic array surface with the knowledge that the light energy will exit at the other optic array surface. Therefore, by using the preferred completely coherent and rigidly maintained parallel alignment of strands illustrated by FIGS. 5 and 6 (the intended distal and proximal optic array surfaces respectively) of a unitary fiber optic array, the user may introduce light energy to a portion or all of the optic array surface 114 and have accurate knowledge and confidence that the light energy would be conveyed by the fiber strands and exit from the optic array surface 112. Conversely, were light energy introduced to the optic array surface 112, the light energy will be conveyed by the optical fibers of the array and will exit from the optic array surface 114.

B. The Optional Gradient Index Lens.

An optional component of the fiber optic sensor is the presence of a Gradient Index or "GRIN" lens joined to and optically aligned with the distal optic array surface of the unitary fiber optic array. GRIN lenses are conventionally known and currently employed to provide far-field focused viewing for optical fibers. A representative embodiment of a GRIN lens is illustrated by FIG. 7.

Figure 7:
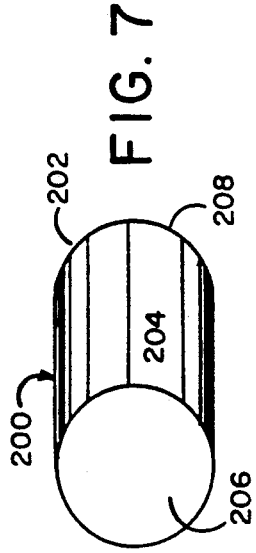
FIG. 7 is an overhead view of a gradient index lens.

As appears in FIG. 7, the GRIN lens 200 is a substantially cylinder-shaped rod 202 having a lens body 204 and two substantially-rounded ends 206 and 208. The dimensions and surface area of the ends 206 and 208 will conform to those of the unitary fiber optic array body and the intended distal optic array end chosen for that sensor construction. Moreover, the pitch, lens diameter, lens length, focal length, design wavelength, refractive index profile, axial index, and other GRIN lens parameters and capabilities may be individually chosen and varied to meet the specific demands of the user or the application—but the lens will typically take physical form as shown by FIG. 7.

Gradient Index or "GRIN" lenses typically are short (1-3 mm) small diameter glass rods that refract light. They are useful for direct attachment or coupling to optical fibers or detectors; and are commonly employed to couple light from one fiber to another. The refractive index of the material forming a GRIN lens varies radially, from a maximum on the axis to a minimum at the outer surface; and a refractive index profile is commonly provided for each GRIN lens to indicate its capabilities. In use, when a ray of light enters the GRIN lens at any angle, the light is continuously directed toward the center of the lens by the refractive index gradient. The path of the light ray forms a sinusoid. The period of the sinusoid is called the pitch, i.e.. the length of rod required for one cycle; and the pitch determines the imaging distance for the lens. Different GRIN lenses provide a variety of different fractional pitches; and thus the distance for far-field viewing and imaging is preselected by the choice of the fractional pitch for the lens. A number of generally available scientific and commercial publications provide a comprehensive description and complete detailed information regarding the workings, manufacture, and capabilities of GRIN lenses. These include the following, each of which is expressly incorporated by reference herein: Oriel Corporation, *Optics & Filters,* Vol. III; Hecht, Optics. 2nd edition, Addison-Wesley Publishing Co., 1987.

GRIN lenses provide a number of advantages for far-field viewing. The generally cylindrical shape of a GRIN lens is easily held and mounted to a unitary fiber optic array; the length of the GRIN lens can be chosen so that a real image is formed at the surface of the lens; and the GRIN lens can be joined to the fiber optic array directly with index matching epoxy, thereby minimizing throughput photon losses.

Figure 15:
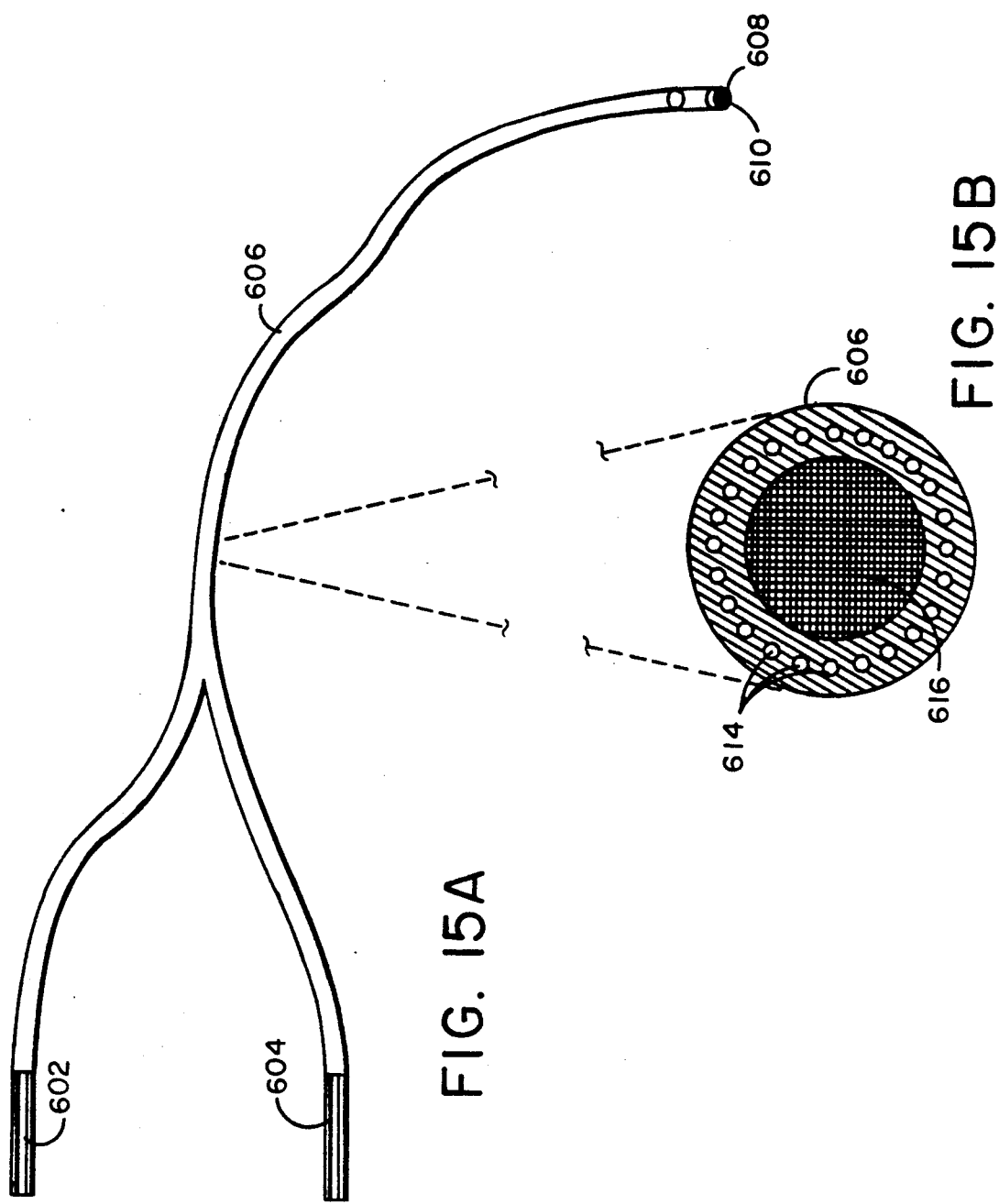
FIGS. 15A and 15B are diagrams of the endoscope and instrumentation embodying a GRIN lens sensor construction of the present invention.

Alternatively, another type of fiber optic instrument, the endoscope, may also be optionally used as a complete substitute for individual optical fiber strands or, more desirably, in bundled form as the unitary optic array itself. Endoscopes of different types and constructions are conventionally known and commercially available [Transcot SA, Geneva, Switzerland; Prescott, R., *J. Med. Primatol.* 5:133-147 (1976)]; and a most preferred type is the fiber bundle endoscope described and illustrated by FIG. 15 hereinafter, with or without the added presence of a fitted GRIN lens.

An endoscope is a optical fiber or preferably a prepared bundle of optical fibers with an eyepiece at one end through which one can view objects as though the eye were placed at the far end of the tube. In addition to their optical characteristics, most endoscopes also contain a fiber optic light guide for illuminating the area to be viewed. Endoscopes are particularly useful and designed for surgical operations; provide visualization capability through a single puncture site; and have an offset eyepiece and a channel through the surgical operating instrument which is inserted directed into that portion of the patient or area to be viewed. Accordingly, it will be recognized and appreciated that endoscopes generally, without regard to their mode of construction or their particular optical features and characteristics, may be usefully employed as the unitary optic array when making the present sensor and detection apparatus; and that endoscopes as such lie within the scope of the present invention.

C. The Thin Film Comprising At Least One Light Absorbing Dye And The Polymerizable Reaction Mixtures For Forming Thin Films.

The Thin Film

The fiber optic sensor of the present invention requires that a substantially uniform and uninterrupted thin film comprising at least one light energy absorbing dye be positioned over, although not necessarily deposited upon, one discrete optical array surface of the unitary fiber optic array. The thin film is a coated layer of carefully controlled and limited thickness; is a structure formed by the polymerization of dye reagents and dye reagents and monomer mixtures including copolymerized dyes, trapped dyes, and adsorbed dyes; and will appear as a discrete, translucent covering having a thickness ranging from about 1-50 microns, a thickness of between 1-15 microns being most preferred.

The particulars of the thin film to be prepared and used will vary with the intended application. If a GRIN lens is present as part of the sensor, then the thin film can be greater in thickness since the focal length is beyond the thin film coating layer. Alternatively, if the sensor is intended for near-field viewing, then a thin film layer of only a few microns is optimal.

Moreover, the thin films themselves may be either transparent or translucent. Since a thickness of only 1-50 microns is permissible, none of the thin films demonstrate any substantial optical density (i.e.. absorbance). Even highly colored materials provide thin films which are virtually transparent because of the short optical path lengths involved.

The formed polymer comprising a thin film coating typically is substantially regular, but some polymer texture or surface irregularity can be present without major consequences to the viewing value of the thin film. The flexibility and tensile strength of the thin film layer will vary markedly and depend upon the polymer used. The variances are provided and controlled by the particular choice from among the conventionally known different polymer compositions; and by selective choice of parameters such as cross-linking concentration, functional group modifications and the like.

Thin Film Positioning

Figure 8:
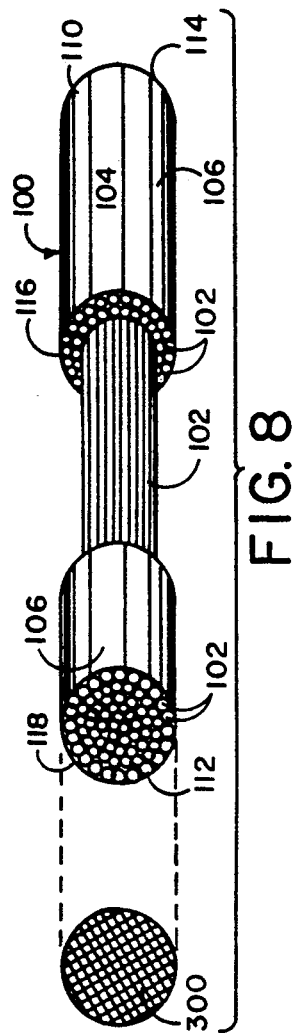
FIG. 8 is an exploded overhead view of a two-component fiber optic sensor embodying the present invention.

The proper positioning of the thin film can be achieved in two different formats and sensor constructions: The simpler format is shown by the exploded illustration of FIG. 8 in which the thin film 300 is placed directly upon the intended distal optic array surface 112 of the unitary fiber optic array 100 as an intimately attached, layered coating. This direct deposition of the thin film results in a two-component construction.

Figure 9:
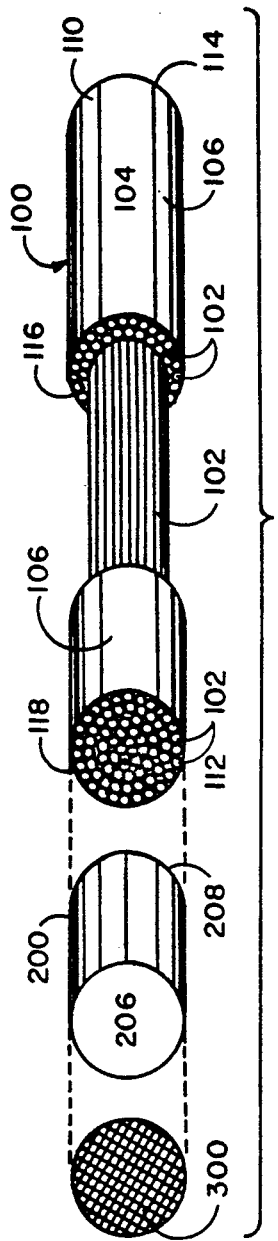
FIG. 9 is an exploded overhead view of a three-component fiber optic sensor embodying the present invention.

The alternative format is shown by the exploded illustration of FIG. 9 in which the thin film is located and tangibly deposited upon the rod end 206 of a GRIN lens 200—which itself via end 208 will be subsequently or has been previously integrally joined and optically aligned with the distal optic array surface 112 of the unitary fiber optic array 100. In this alternative format, the thin film is in intimate contact and is deposited upon the GRIN lens alone; and is only via the GRIN lens optically positioned and aligned to the distal optic array surface 112 of the unitary fiber optic array 100. This results in a three-component sensor construction.

While the two-component format construction is preferred for near-field viewing; the optional inclusion of the GRIN lens provides for far-field viewing of the sample and its environs. Both of these formats and thin film positionings is within the scope of the present invention.

The Light Energy Absorbing Dyes

At least one light energy absorbing dye is contained within the thin film positioned over the intended distal array surface of the unitary fiber optic array. If more than one dye reagent is employed, it is more desirable that each dye formulation provide and present individual spectral properties that do not or minimally overlap the other dye or dyes held within the thin film coating.

Each light energy absorbing dye formulation or composition will react with only one ligand or analyte of interest. Moreover, each dye will then show evidence of such reactive contact by either absorbing and reflecting a portion of the light energy; or, alternatively, by absorbing light energy and then subsequently emitting light energy of a different wavelength in return. Such reflected or emitted light energy is conveyed from the thin film coating positioned over the distal optic array surface; and such conveyed light will emerge from the proximal optic array surface for detection and measurement.

The dyes which may be employed and disposed individually within the thin film positioned over one optic array surface of the fiber optical array are all conventionally known and often commercially available. The present invention intends that all the commonly useful properties and capabilities of the various classes of light energy absorbing dyes be employed as needed or desired for the specific use or application. Merely illustrative of the many different dyes are those fluorophores, fluorescent enzyme substrates, fluorescent antibody conjugates, and chromophores listed below within Tables I and II respectively.

TABLE I

| Compounds | Excitation Wavelength (range or maximum) | Fluorescence emission range (max) |
| --- | --- | --- |
| A. Fluorophores | | |
| Eosin | 520–530 nm | 530–580 nm (550 nm) |
| TRITC-amine | 555 nm | 570–610 nm (590 nm) |
| Quinine | 330–352 nm | 382–450 nm |
| Fluorescein W | 488–496 nm | 530 nm |
| Acridine yellow | 464 nm | 500 nm |
| Lissamine Rhodamine B Sulfonyl Chloride | 567 nm | 580 nm |
| Erythroscein | 504 nm | 560 nm |
| Ruthenium (tris, bipyridium) | 460 nm | 580 nm |
| Texas Red Sulfonyl Chloride | 596 nm | 615 nm |
| B-phycoerythrin | 545, 565 nm | 575 nm |
| Nicotinamide adenine dinucleotide (NADN) | 340 nm | 435 nm |
| Flavin adenine dinucleotide (FAD) | 450 nm | 530 nm |
| Carboxy Seminaphthorhodafluor | 587 nm | 640 nm |
| Naphthofluorescein | 594 nm | 663 nm |
| B. Fluorescent Enzyme Substrates | | |
| Fluorescein mono-B-D-galacto-pyranoside | 452 nm | 518 nm |
| Resorufin B-d-glucuronide | 468 nm | 584 nm |
| 8-acetoxypyrene -1,3,6 - trisulfonic acid trisodium salt | 368 nm | 391 nm |
| Coenzyme A (1-pyrene butanoic acid) ester | 339 nm | 377 nm |
| Fluo-3; free acid [Molecular Probes, Eugene, CA] | 506 nm | 526 nm |
| Quin-2, tetrapotassium | 352 nm | 492 nm |
| C. Fluorescent Antibody Conjugates | | |
| Texas Red goat anti-mouse Fg G conjugates | 590 nm | 615 nm |
| Protein A fluorescein conjugates | 480 nm | 520 nm |
| Anti-Atrazine fluorescein Conjugates | 480 nm | 520 nm |
| Anti-digoxin Texas Red Conjugates | 590 nm | 615 nm |

TABLE II

| Chromophores | Range (max) |
| --- | --- |
| Iron-salicylate complex | 530 nm |
| Indamine dye | 590 nm |
| INT formazon dye | |
| Hopkins-Cole dye | 560 nm |
| Quinone-imine dye | 500 nm |
| Fe (SCN)$^{+2}$ | 460 nm |
| Malachite Green | 620 nm |
| 4-bromo A-23187, freeacid | 340 nm |
| Cresol red | 415 nm, acid; 570 nm, base |
| diphenylcarbazone disulphonic acid | 575 nm |
| Chrome bordeaux B | 575 nm |
| Calmagite | 650 nm |
| Ninhydrin dye | 650 nm |

It will be recognized and appreciated also that the range, variety, and diversity of light energy absorbing dyes, dye formulations, and dye mixtures comprising the thin film is not dependent upon a single light source or light energy supply in order to be effective. Although light energy of determinable wavelengths is desirably provided by electrical light sources—that is, light emitting diodes (LED's), lasers, laser diodes and filament lamps whose bands of light energy are typically controlled and selected by filters, diffraction gratings, polarizing filters; or alternatively broken into various broad wavelengths of light energy via prisms, lenses, or other optical/spectral articles, these are not exclusively the only source of useful light energy. Clearly, in various applications and circumstances chemical light energy, bioluminescence, and other less typical or conventionally employed light energy sources are deemed to also be useful. Accordingly, neither the true source, nor the nature of light energy photons, nor the manner in which they are conveyed or otherwise caused to be created is of importance or consequence.

In addition, the dye individually may comprise other materials such as enzymes, or antibodies, or chemical compounds for photo reactive contact. Thus each dye individually within the thin film may in fact be formulated as a mixture of both light emitting and light absorbing dyes; and also comprise a variety of other light energy sensitive compounds made conventionally which are able to interact with specific dye properties. Merely exemplifying the nature of such multiple dye formulations and combinations are those described and claimed within copending U.S. Pat. No. 5,114,864 issued May 19, 1992 as well as the compositions described within U.S. Pat. No. 4,822,746 issued Apr. 18, 1989—the texts of which are individually expressly incorporated by reference herein.

Polymerizable Thin Film Reagent Mixtures

When forming and depositing the thin film coating at the chosen location, it is desirable that the dye formulations be combined with monomer compounds to form a polymerizable reagent mixture. Among the conventional practices, a variety of different polymerization processes are known, including thermal techniques, photoinitiated methods, ionization methods, plasma methods, and electroinitiation procedures. These different methodologies are exemplified by the following publications, the text of each being expressly incorporated by reference herein. Thermal methods: Graham et al., *J. Org. Chem.* 44:907 (1979); Stickler and Meyerhoff, *Makromal. Chem.* 159:2729 (1978); and Brand et al., *Makromol. Chem.* 181:913 (1980). Fonization methods: A. Chapiro, *Radiation Chemistry of Polymer Systems* Chapter IV, Wiley—Intersciences, Inc., New York, 1962; J. E. Wilson, *Radiation Chemistry of Monomers, Polymers, and Plastics,* chapters 1-5, Marcel Dekker, New York, 1974. Plasma Methods: Yasuda, W. and T. S. Hsu, *J. Polym. Sci. Polym., Chem. Ed.* 15:81 (1977); Tibbett et al., *Macromolecules* 10:647 (1977). Electroinitiation methods: Pistoria, G. and O. Bagnarelli, *J. Polym. Sci. Polym. Chem. Ed.* 17:1001 (1979); Philips et al., *J. Polym. Sci. Polym. Chem. Ed.* 15:1563 (1977); and Odian, G., *Principles of Polymerization,* 3rd Edition, Wiley-Interscience, Inc., New York.

The preferred method of thin film preparation and deposition is via the process of thermal polymerization; and employs one or more temperature activated monomer preparations in admixture with one or more prechosen light energy absorbing dyes as a polymerizable formulation [as described in Munkholm et al., *Anal. Chem.* 58:1427 (1986); and Jordan et al., *Anal. Chem.* 59:437 (1987)]. Such monomer preparations typically comprise solutions of several monomers in admixture and a fixed concentration of at least one light energy absorbing dye conjugated to an organic carrier which can be chemically cross-linked. A representative listing of different monomer compositions suitable for preparing a reaction admixture which subsequently can be thermally polymerized are given by Table III; an illustrative listing of conjugated dyes ready for admixture and photopolymerization is given by Table IV below.

TABLE III

| A. Monomers |   |
|---|---|
| acrylamide | |
| N,N - methylene bis (acrylamide) | |
| hydroxyethylmethacrylate | |
| styrene | |
| vinyl acetate | |
| (N- (3-aminopropyl) methacrylamide hydrochloride [Kodak, Inc.] | |
| B. Comonomer with dimethylsiloxane | |
| (acryloxypropyl) methyl | (15-20%) |
| (aminopropyl) methyl | (3-5%) |
| (methacryloxypropyl) methyl | (2-3%) |
| C. T-structure polydimethylsiloxanes | |
| methacryloxypropyl | (25-50%) |
| vinyl | (50-75%) |

TABLE IV

| Conjugated dye |
|---|
| acryloyl fluorescein |
| acryloyl rhodamine |
| acryloyl eosin |
| phenol red |
| acryloyl 8-hydroxypyrene 1,3 disulfonic acid |
| acryloyl seminaphthorhodafluor |
| acryloyl seminaphthofluorescein |

It will be appreciated that the listings of Table III and Table IV are merely representative of the many different substances which can be usefully employed in admixture with one or more light energy absorbing dyes to form the thin film coating. In addition, the scientific and industrial literature provides many alternative monomer preparations and admixtures which are also suitable for use in making the present invention; and the dyes may be incorporated into the polymer thin film by alternative means and techniques such as entrapment, adsorption, electrostatic binding, and the like. Accordingly, all of these conventionally known preparations are considered to be within the scope of the present invention.

II. A Preferred Sensor for Concurrently Viewing the Sample and Optically Measuring pH To demonstrate a most desirable method for making the unique fiber optic sensor comprising the present invention as well as to illustrate the utility and effectiveness of the sensor within a fully constructed apparatus, a detailed description of the manipulative steps for making a preferred sensor which allows the user to measure pH and directly view the sample concurrently is presented. It will be expressly understood, however, that the detailed description which follows hereinafter is merely illustrative and representative of the many different kinds of sensors which can be made having the capability to observe the sample and its environs concurrent with the ability to detect and accurately measure ligands or analytes by optical determinations.

Materials: All materials and reagents were commercially obtained. These included: potassium phosphate, monobasic and diabasic [Fisher]; N,N,N$^1$,N$^1$-tetramethylethylenediamine (TEMED) [Biorad]; ammonium persulfate [Kodak]; hydroxyethyl methacrylate (HEMA) and ethyleneglycol dimethacrylate (EGDMA) [Polysciences, Inc.]; acetone and n-propanol [Baker]. All other materials were purchased from Aldrich Chemical Co. All reagents were used without further purification.

Imaging fiber optic arrays of 200, 350, and 500 μm diameter and 0.3 m length were obtained from commercial sources and were terminated with AMP Incorporated connectors on one end (proximal). The proximal end was polished using a polishing bushing; and the fiber distal tip was polished using a Fiberoptics, Inc. polishing kit. The polished distal end was cleansed with conc. $H_2SO_4$.

Sensor Preparation Procedure:

Surface Silanization with 3-(trimethoxysilyl) propyl methacrylate. A 10% (v/v) solution of 3-(trimethoxysilyl) propyl methacrylate in dry acetone was prepared. The fiber optic arrays were individually submerged in this solution for a minimum of 2 hours, rinsed with acetone and used immediately.

Dye Preparation. Acryloylfluorescein was prepared by mixing dry acetone (20 ml); fluoresceinamine isomer I (180 mg, 0.518 mmol); acryloyl chloride (45 μl, 0.55 mmol); and then allowing the reaction mixture to stir for 1 hour in the dark. The precipitate formed by the reaction was then filtered and washed with acetone, followed by addition of dichloromethane (volume not critical).

HEMA/Acryloylfluorescein/Ammonium persulfate polymerization solution. A stock solution was prepared formulated of 5 ml hydroxyethyl methacrylate (opthalmic grade); 5 ml 0.1 M phosphate buffer pH 6.8; 100 μl ethyleneglycol dimethacrylate (EGDMA); and 0.5 ml of dye solution (50 mg acryloylfluorescein in 100 ml propanol).

Polymerization Conditions: 1 ml of the stock polymerization solution is added to a 3 ml vial and deoxygenated by bubbling with $N_2$ for 15 minutes. The vial is set in a 55° C. water bath, at which time 1 mg ammonium persulfate is added, and the distal optic array surface of each fiber optic array are inserted. Polymerization of the mixture is allowed to occur with constant stirring under $N_2$. The ends of the fiber array are removed just prior to reaction completion—as determined by a significant increase in viscosity. Polymerization times may vary from batch to batch. Typically, polymerization and formation of the thin film is complete within 10 minutes. However, if this does not occur, 10μl TEMED is then added; and the polymerization reaction is complete within 2 additional minutes [Munkholm et al., Anal. Chem. 58:1427 (1986)]. After polymerization, the thin films of the fiber optic arrays are each allowed to cure for approximately 2 hours, after which they are soaked in phosphate buffer for at least 12 hours to ensure no unbound dye has remained in the polymer layer of each thin film coating.

The process of thermal polymerization is initiated in the bulk solution in which the functionalized fiber optic array ends are submerged. Parameters such as temperature, concentration of monomer, crosslinker, and initiator are held constant, however, reaction times may vary significantly from batch to batch. For this reason, thermal polymerizations must be monitored carefully to assure that the fiber array ends are removed from the reaction mixture just prior to completion. More specifically the fiber array end must be removed just as the polymer begins to appear viscous as determined by the visible slowing of a magnetic stir bar or by inserting a small stirring rod and visually observing the solution's viscosity as it is withdrawn from the reaction medium.

After polymerization, the fiber arrays are inspected to assess the uniformity and thickness of the polymer layer forming the thin film coating. The pH sensitive layer must be thin, ideally, less than 10 μm. A thicker film results in longer response times, and may hinder imaging capabilities as the focal point of the fiber array is at the optic array surface. The polymer layer must also be fairly uniform and uninterrupted for optimal measuring capabilities.

Figure 10:
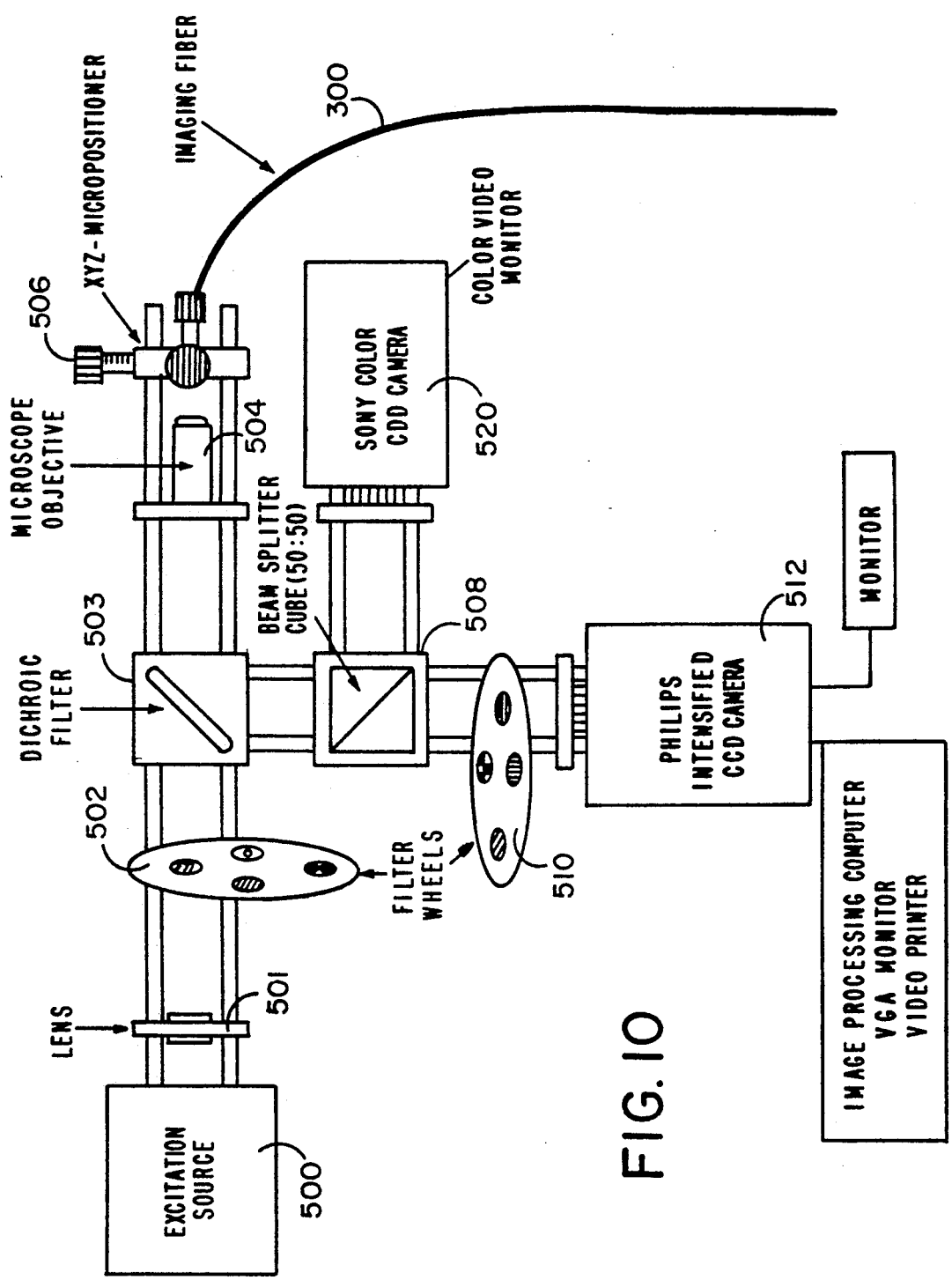
FIG. 10 is a schematic representation of an apparatus suitable for concurrent viewing and chemical sensing using the sensor of FIG. 8.

Apparatus: Sensor measurements and visual imaging were performed using the apparatus shown schematically in FIG. 10. White light from a 75 Watt, 1.0 mm arc, mercury-xenon lamp 500 (Hamamatsu) is columnated; focused by a lens 501; passed through a 485 nm excitation filter 502 (Corion); and focused on the proximal end 114 of the imaging fiber optic sensor 300 with a 10X microscope objective 504 (Rolyn Optics). The imaging fiber optic sensor 300 is held in an xyz-micropositioner 506 (Spindler and Hoyer), which allows for fine focusing. Excitation light (485 nm) is transmitted down the fiber array, and illuminates the thin film of the sensor which fluoresces in proportion to analyte concentration. The returning fluorescence light is reflected 90° by the dichroic filter 503; passed through a beam splitter cube 508 (50/50, Spindler and Hoyer); filtered at the appropriate emission wavelength (520 nm) by filter wheel 510; and detected by the CCD camera 512. Ratiometric measurements are obtained by monitoring fluorescence at 525 nm while switching between two excitation filters, 485 nm and 430 nm, using the filter wheel 510. The Philips CCD camera 512 contains a 256×256 photosensitive element and is coupled to an electronic intensifier; which in turn is connected to a 386 personal computer having a 512-8 Video Frame Grabber graphic card (high Res Technologies) that digitizes and processes the video image. Visual imaging is achieved by using a SONY color CCD video camera 520 to collect the light which is reflected 90° by the beam splitter cube 508. (Note: Simultaneous visual imaging and chemical sensing may also be performed using a single CCD camera by removing the second color camera and the beam splitter cube.) Illumination for visual imaging purposes is achieved either by rotating the excitation filter wheel to an empty position (using neutral density filters as necessary); or by illuminating the sample and its environs at the distal end of the fiber sensor with an independent light source.

Figure 11:
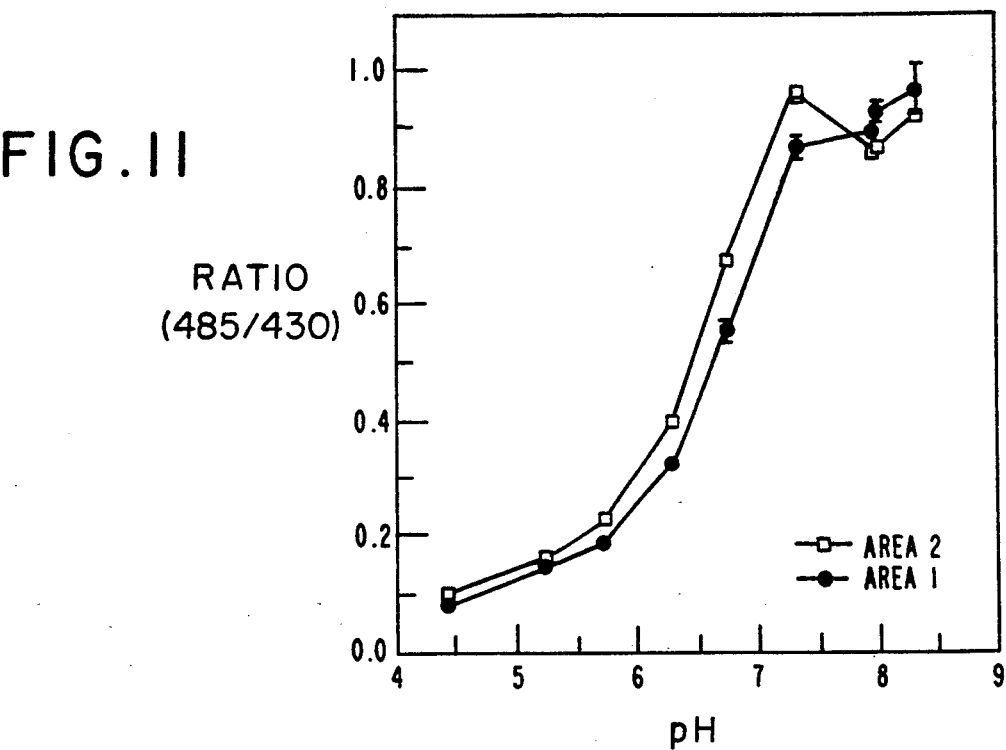
FIG. 11 is a graph illustrating pH titration curves for two areas of a 350 $\mu$m sensor having a thin film comprised of poly HEMA/fluorescein.

Empirical Measurements and Results: To determine pH sensitivity, the sensor was submerged in phosphate buffer solutions of varying pH and fluorescence images were captured with a CCD camera. Fluorescence was monitored at 525 nm using both 430 and 485 nm excitation. Data are digitized and analyzed to yield a final ratiometric reading (485 nm/430 nm). The titration curves for two regions on the surface of a 350 μm fiber coated with polyHEMA/fluorescein are shown in FIG. 11. The two curves are almost identical, both having a $pK_3$ of approximately 6.5 pH units.

Figure 12:
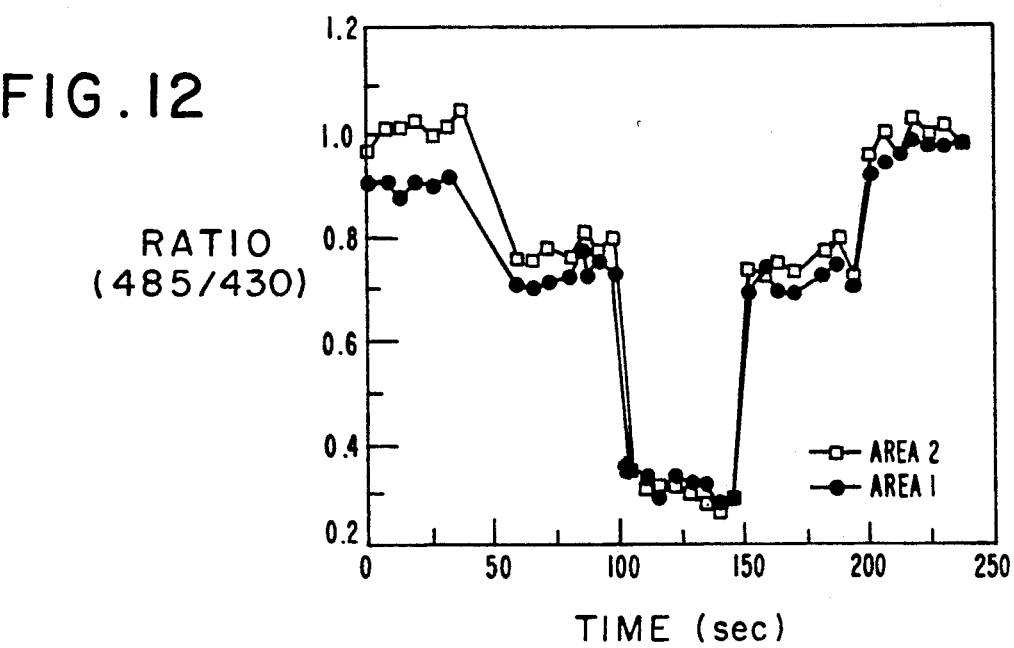
FIG. 12 is a graph illustrating the response of a 350 $\mu$m sensor with a poly HEMA/fluorescein thin film as a function of pH.

It is noted that there is a significant loss of fluorescent signal over time; therefore, ratiometric readings are used as an internal calibration which obviates accounting for the effects of photobleaching or loss of dye during measurements. FIG. 12 illustrates the reproducibility of readings when the fiber sensor end is submerged in buffers of varying pH. The thin film of the sensor is successfully cycled through pH 7.6, 6.8, 6.0, 6.8, and 7.6, respectively; and ultimately returns to its original signal level. Again, there is an excellent correlation between the two areas measured.

Figure 13:
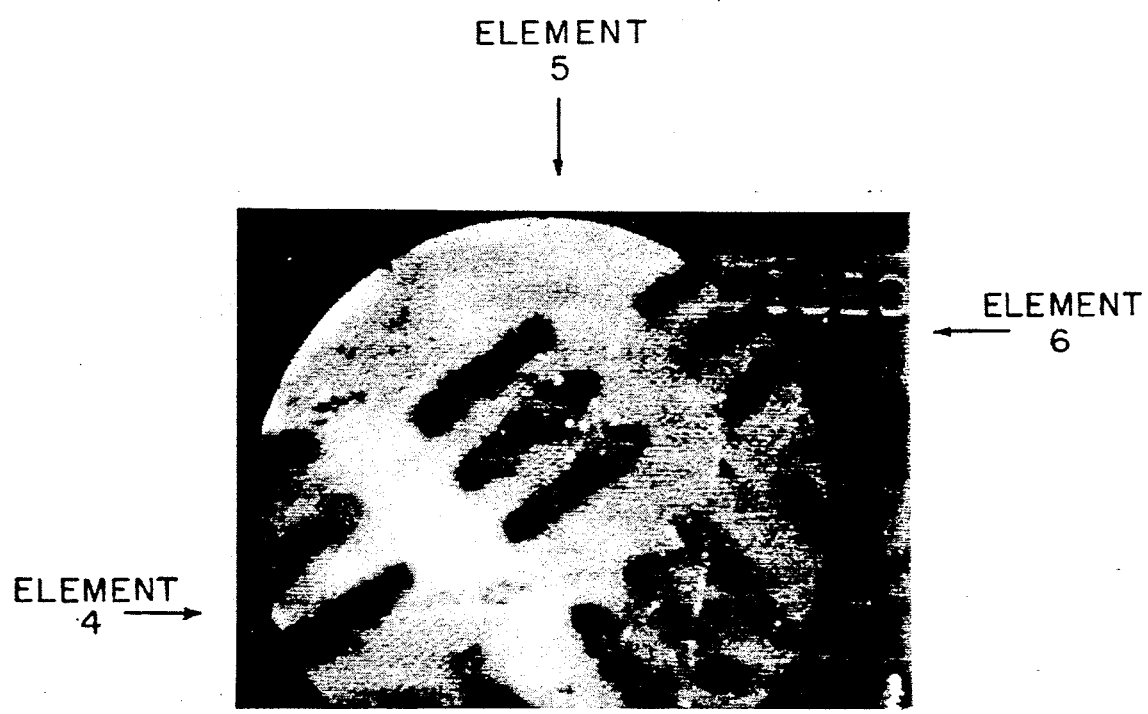
FIG. 13 is a photograph of a Resolution Target image conveyed through a 350 $\mu$m sensor having a poly HEMA/fluorescein thin film.

The visual imaging capabilities of the thin film sensor are demonstrated by viewing a standard Air Force Resolution Target (Newport). The photograph shown in FIG. 13 is the observed image of the target taken between the pH measurements (6.0-7.6) reported above. The thin film sensor end was removed from the buffer solution and held in contact with the target, which was illuminated with a flashlight. The visual image conveyed by the sensor was captured by the second CCD camera, and a picture was taken of the image on the monitor. The line pairs photographed are from Group 4, elements 4,5, and 6, which are 22.62, 25.39, and 28.51 line pairs/mm respectively. The highest resolution of the group is found in element 6, which corresponds to a line width of 17.54 $\mu$m. It is apparent from the visual image that this particular sensor has resolving capabilities better than 17 $\mu$m. Ultimately, the resolving capabilities of the sensor are dependent on the size of the individual optical fiber elements which comprise it. In this case, the sensor is a 350 $\mu$m fiber array with thousands of individual optical fibers strands each having a diameter of 2 to 3 $\mu$m.

Figure 14:
FIG. 14 is a photograph of a sea urchin eggs image conveyed through a 500 $\mu$m sensor having a thin film sensitive for pH.

From these data, the ability to combine two useful capabilities using a single fiber optic sensor is demonstrated. This technique has many potential applications as the sensitive thin film coating may be changed to measure a number of different ligands or analytes. Potential applications include measuring cell surface chemistry while correlating to morphological changes. FIG. 14 shows several sea urchin eggs (approximately 80 $\mu$m in diameter) as viewed through a 500 $\mu$m imaging fiber coated with a pH sensitive layer. A single endoscope may also be used to view and measure during a clinical procedure (e.g. view a thrombus and simultaneously measure the effectiveness of angioplasty by sensing $CO_2$ or $O_2$).

III. A GRIN Lens Sensor

Another mode of sensor construction employs a unitary optic fiber array in combination with a GRIN lens having a thin film coating. An endoscope fitted with a GRIN lens was obtained from Transcot SA (Geneva, Switzerland) and coated with a pH sensitive thin layer in a manner similar to the method described previously herein. Chemical sensing measurements and visual imaging were performed using apparatus substantially similar to that schematically illustrated by FIG. 10 but now having a second illumination source which is coupled to the picture element bundle as shown by FIGS. 15A and 15B respectively.

Note that FIG. 15A reveals an illuminating fiber bundle 602 and a picture element bundle 604 which are joined together to form a common unitary array 606. A GRIN lens 608 coated with a thin film 610 is in aligned optic position and fitted to the common unitary array 606. FIG. 15B illustrates an enlarged cross-sectional view of the common unitary array 606; and reveals the detailed location and positional relationship of the illuminating fibers 614 of the illuminating fiber bundle 602 a well as the picture elements 616 of the picture element bundle 604.

Figure 16:
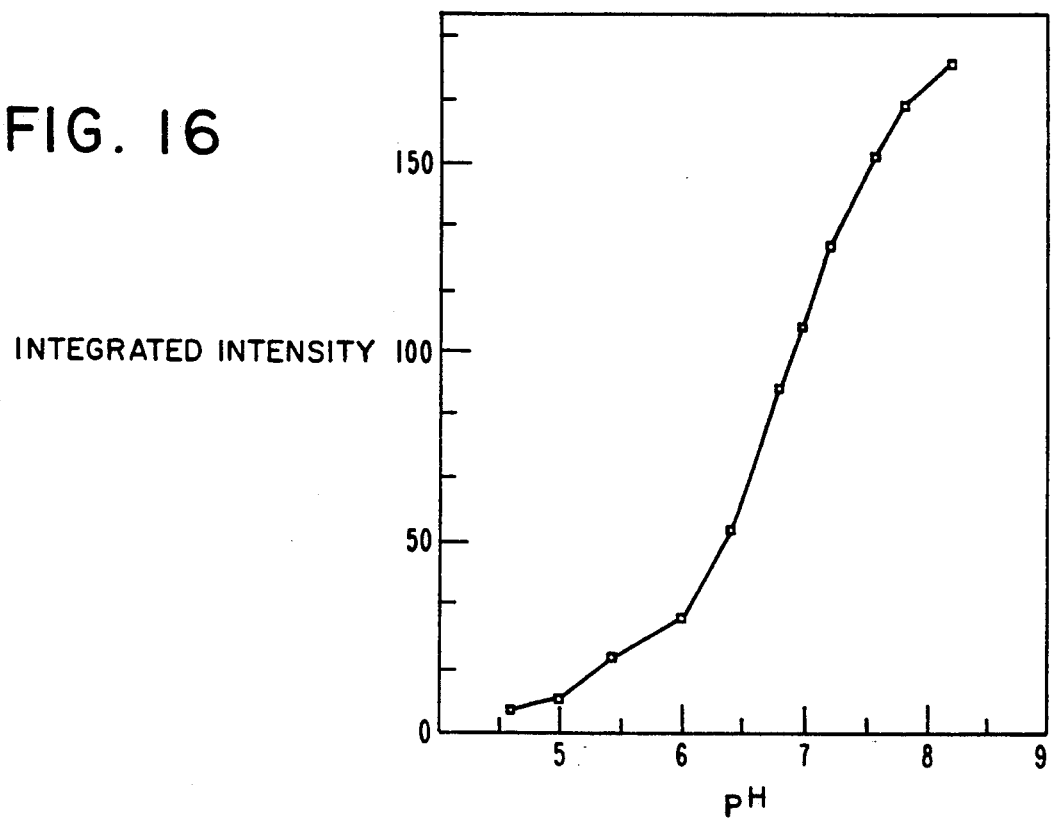
FIG. 16 is a graph illustrating the pH titration curve for the endoscope of FIG. 15 coated with a thin film comprising fluorescein/poly HEMA.
Figure 17:
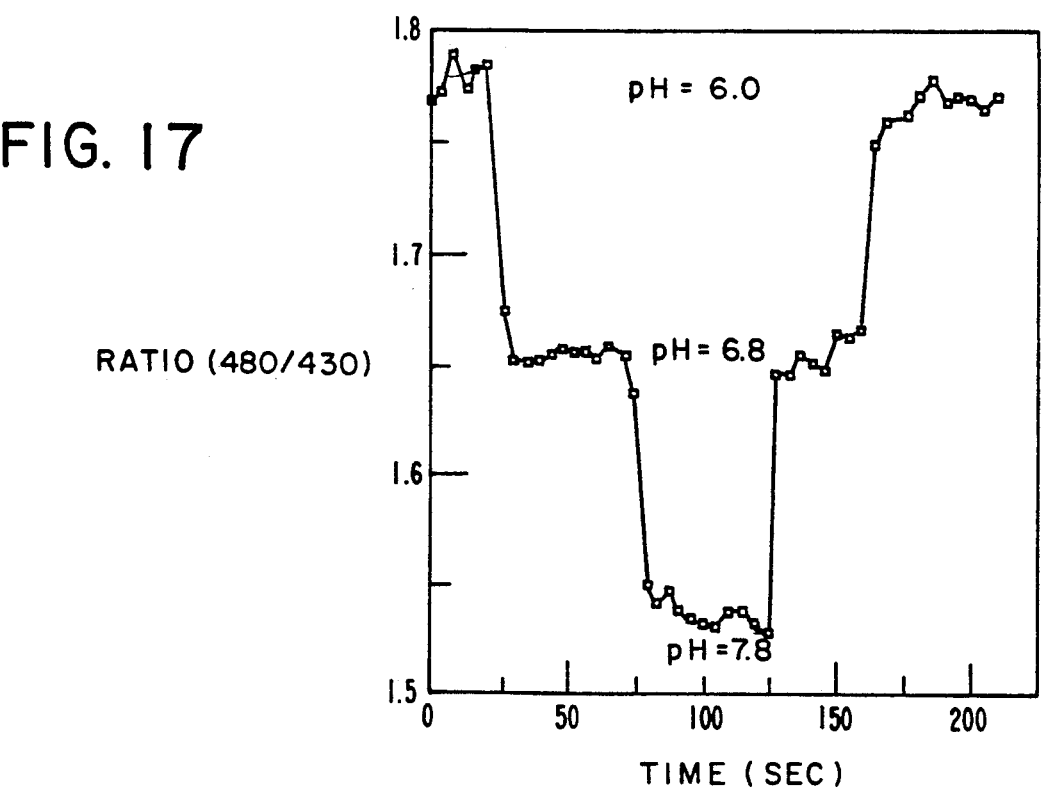
FIG. 17 is a graph illustrating the ratiometric response curve (Ratio 480/430) for the endoscope of FIG. 15 coated with a thin film comprising fluorescein/poly HEMA.
Figure 18:
FIG. 18 is a photograph illustrating the visual image of 1.5 mm sized letter "E" when viewing through the endoscope of FIG. 15 coated with a thin film comprising fluorescein/poly HEMA.

The pH sensitivity of this GRIN lens sensor is demonstrated by FIGS. 16 and 17 respectively. FIG. 16 shows the pH titration curve for the sensor coated with a thin film of fluorescein/polyHEMA while FIG. 17 shows a ratiometric response curve for changes of pH over time. It will be noted and appreciated that the chemical sensing capacity of the thin film does not compromise the viewing or visual imaging capabilities of the sensor. This is shown by FIG. 18 which provides a visual image of a 1.5 mm sized letter "E" as viewed through the thin film coating positioned on the GRIN lens of the endoscope. The end tip of the sensor was approximately 2-3 mm distance from the letter "E" object being viewed.

The present invention is not to be restricted in form nor limited in scope except by the claims appended hereto.

What we claim is:

1. A fiber optic sensor useful in an apparatus for concurrently viewing the environs of and optically detecting at least one ligand of interest of a fluid sample, said fiber optic sensor being comprised of:
   a preformed, unitary fiber optic array comprising a plurality of individually clad, fiber optical strands disposed co-axially along their lengths and having two discrete optic array ends each of which is formed of multiple strand end faces, said preformed, unitary fiber optic array being of determinable configuration and dimensions, said two discrete ends of said preformed, unitary fiber optic array presenting two discrete optic array surfaces for introduction and conveyance of light energy; and
   a substantially uniform and uninterrupted thin film comprising at least one light energy absorbing dye positioned over one of said discrete optic array surfaces of said preformed, unitary fiber optic array, said thin film having a thickness ranging from about 1-50 microns, each light energy absorbing dye of said thin film reacting with a ligand of interest in a manner correlatable with an optical determination.

2. The fiber optic sensor as recited in claim 1 further comprising a gradient index lens joined to and optically aligned with one end of said unitary fiber optic array.

3. The fiber optic sensor as recited in claim 1 wherein said thin film comprises at least two different dyes.

4. The fiber optic sensor as recited in claim 1 wherein the wavelength of said light energy absorbed by said dye is selected from the group consisting of infrared, visible and ultraviolet wavelengths.

5. The fiber optic sensor as recited in claim 1 wherein said dye is selected from the group consisting of fluorophores, fluorescent enzyme substrates and fluorescent antibody conjugates.

6. The fiber optic sensor as recited in claim 1 wherein said dye is a chromophore.

7. An apparatus for concurrently viewing the environs of and optically detecting at least one ligand of interest of a fluid sample, said apparatus comprising:
   a fiber optic sensor comprised of
   (a) a preformed, unitary fiber optic array comprising a plurality of individually clad, fiber optical strands disposed co-axially along their lengths and having two discrete optic array ends each of which is formed of multiple strand end faces, said preformed, unitary fiber optic array being of determinable configuration and dimensions, said two discrete ends of said unitary fiber optic array presenting two discrete optic array surfaces for introduction and conveyance of light energy, (b) a substantially uniform and uninterrupted thin film comprising at least one light energy absorbing dye positioned over one of said discrete optic array surfaces of said preformed, unitary fiber optic array, said thin film having a thickness ranging from about 1-50 microns, each light energy absorbing dye of said thin film reacting with one ligand of interest in a manner correlatable with an optical determination;

means for placing said thin film of said fiber optic sensor into reactive contact with a fluid sample;

means for introducing light energy to said thin film of said fiber optic sensor for illumination of said light energy absorbing dye;

means for detecting emerging light energy from said illuminated thin film of said fiber optic sensor, said detected emerging light energy serving as an optical determination for a ligand of interest in the fluid sample;

means for illuminating the fluid sample and its environs; and means for concurrently viewing the fluid sample and its environs through said thin film of said fiber optic sensor.

8. The apparatus as recited in claim 7 wherein said fiber optic sensor further comprises a gradient index lens joined to and optically aligned with one end of said unitary fiber optic array.

9. The apparatus as recited in claim 7 further comprising automated means for concurrently introducing light energy and detecting emerging light.

10. The apparatus as recited in claim 7 wherein said detected emerging light is visualized as a discrete image.

11. The apparatus as recited in claim 7 further comprising a computer controlled imaging and data processing system.

12. A method for concurrently viewing the environs of and optically detecting at least one ligand of interest of a fluid sample, and method comprising the steps of:
obtaining a fiber optic sensor comprised of
(a) a preformed, unitary fiber optic array comprising a plurality of individually clad, fiber optical strands disposed co-axially along their lengths and having two discrete optic array ends each of which is formed of multiple strand end faces, said preformed, unitary fiber optic array being of determinable configuration and dimensions, said two discrete ends of said preformed, unitary fiber optic array presenting two discrete optic array surfaces for introduction and conveyance of light energy,
(b) a substantially uniform and uninterrupted thin film comprising at least one light energy absorbing dye and positioned over one of said discrete optic array surfaces of said preformed, unitary fiber optic array, said thin film having a thickness ranging from about 1-50 microns, each light energy absorbing dye of said thin film reacting with one ligand of interest in a manner correlatable with an optical determination;

placing said thin film of said fiber optic sensor into reactive contact with a fluid sample;

introducing light energy to said thin film of said fiber optic sensor for illumination of said light energy absorbing dye;

detecting emerging light energy from said thin film of said fiber optic sensor, said detected emerging light energy serving as an optical determination for a ligand of interest in the fluid sample;

illuminating the fluid sample and its environs; and concurrently viewing the fluid sample and its environs through said thin film of said fiber optic sensor.

13. The method as recited in claim 12 wherein said detecting and viewing is made in-vivo.

14. The method as recited in claim 12 wherein said detecting and viewing is made in-vitro.

15. The method as recited in claim 12 wherein said detecting and viewing is made using an automated imaging and data processing system.

* * * * *

UNITED STATES PATENT AND TRADEMARK OFFICE
CERTIFICATE OF CORRECTION

PATENT NO.    : 5,298,741  
DATED         : March 29, 1994  
INVENTOR(S)   : Walt et al.

It is certified that error appears in the above-identified patent and that said Letters Patent is hereby corrected as shown below:

Column 1,  
Line 5, after the Title, insert the following:

-- This invention was made with government support under GM48142 awarded by the National Institutes of Health. The government has certain rights in the invention. --

Signed and Sealed this

Sixth Day of August, 2002

Attest:

Attesting Officer

JAMES E. ROGAN  
Director of the United States Patent and Trademark Office